(12) United States Patent
Norén et al.

(10) Patent No.: US 8,073,540 B2
(45) Date of Patent: Dec. 6, 2011

(54) IMPLANTABLE HEART STIMULATING DEVICE WITH STIMULATION RATE OPTIMIZATION

(75) Inventors: Kjell Norén, Solna (SE); Kenth Nilsson, Akersberga (SE)

(73) Assignee: St. Jude Medical AB, Jarfalla (SE)

(*) Notice: Subject to any disclaimer, the term of this patent is extended or adjusted under 35 U.S.C. 154(b) by 229 days.

(21) Appl. No.: 12/305,552

(22) PCT Filed: Jun. 21, 2006

(86) PCT No.: PCT/SE2006/000757
§ 371 (c)(1),
(2), (4) Date: Dec. 18, 2008

(87) PCT Pub. No.: WO2007/149019
PCT Pub. Date: Dec. 27, 2007

(65) Prior Publication Data
US 2009/0210023 A1    Aug. 20, 2009

(51) Int. Cl.
*A61N 1/365* (2006.01)
(52) U.S. Cl. .......... 607/18; 607/9; 607/17; 607/19; 607/24; 607/25
(58) Field of Classification Search .......... 607/9, 17–19, 607/24–25
See application file for complete search history.

(56) References Cited

U.S. PATENT DOCUMENTS

| | | | |
|---|---|---|---|
| 5,065,759 A | 11/1991 | Begemann et al. | |
| 5,154,170 A | 10/1992 | Bennett et al. | |
| 5,282,839 A * | 2/1994 | Roline et al. | 607/19 |
| 5,549,650 A * | 8/1996 | Bornzin et al. | 607/24 |
| 5,562,711 A | 10/1996 | Yerich et al. | |
| 5,792,198 A | 8/1998 | Nappholz | |
| 6,055,454 A | 4/2000 | Heemels | |
| 6,141,590 A * | 10/2000 | Renirie et al. | 607/20 |
| 6,249,700 B1 | 6/2001 | Alt | |
| 6,275,733 B1 | 8/2001 | Park et al. | |
| 6,336,048 B1 | 1/2002 | Bonnet | |
| 6,725,093 B1 | 4/2004 | Ben-Haim et al. | |
| 2003/0153953 A1 | 8/2003 | Park et al. | |

OTHER PUBLICATIONS

"Sensors for Rate Responsive Pacing," Dell'Orto et al, Indian Pacing and Electrophysiology Journal, vol. 4, No. 3 (2004) pp. 137-145.

* cited by examiner

*Primary Examiner* — Niketa Patel
*Assistant Examiner* — Rex R Holmes
(74) *Attorney, Agent, or Firm* — Schiff Hardin LLP

(57) ABSTRACT

An implantable heart stimulating device has a stimulation pulse generator that emits stimulation pulses at an adjustable stimulation rate, an activity sensor that emits an activity signal in response to detected activity of the patient, and a physiological parameter sensor that generates a physiological sensor signal in response to a detected physiological parameter. The activity and physiological sensor signals are supplied to a control arrangement that sets the stimulation rate for the stimulation pulse generator by executing a stimulation rate algorithm dependent on those signals. In the stimulation rate algorithm, if the physiological signal indicates an emotional stress on the part of the patient, the stimulation rate is increased to an adjustable emotional stress rate level, and if no increase in the activity signal occurs during a predetermined time period following the stimulation rate increase, the stimulation rate is decreased.

8 Claims, 4 Drawing Sheets

IMPLANTABLE HEART STIMULATING DEVICE WITH STIMULATION RATE OPTIMIZATION

BACKGROUND OF THE INVENTION

1. Field of the Invention

The present invention relates to an implantable heart stimulating device wherein the stimulation rate is optimized dependent on sensed information.

2. Description of the Prior Art

High blood pressure, hypertension, is abnormally high blood pressure that puts stress on the tissue and organs in the body. Over time, high blood pressure can damage heart, lungs, brain, kidneys, eyes and blood vessels, as well as leading to heart disease, heart attack or stroke. High blood pressure usually does not cause symptoms and is often known as the "Silent Killer". Organs and tissues can be damaged by high blood pressure without any felt symptoms until advanced stages of damage. Symptoms such as headache, blurry vision, abdominal and chest pain, shortness of breath, anxiety and dizziness may be experienced if the blood pressure reaches extreme levels. Many are symptoms usually not related to hypertension.

Blood pressure measurements are read as two numbers, the systolic and diastolic pressure. The higher number is called systolic pressure and the lower number is called diastolic pressure. Normal range of blood pressure is 120/80. High blood pressure is defined when the systolic pressure is greater than 140 and/or diastolic pressure is greater than 90.

In addition to thickening arteries, high blood pressure can cause hypertrophy of the heart. Hypertrophy is the enlargement of the heart because the heart is working too hard. This increases the risk for heart failure and arrhythmias. High blood pressure directly increases the risk of coronary heart disease (which leads to heart attack) and stroke, especially when it is present with other risk factors.

Although there is no single cause for high blood pressure, there are several risk factors that may affect blood pressure. There are two types of risk factors for high blood pressure: factors beyond control such as family history and age, and life style factors that can be controlled. The life style factors may include overweight, alcohol, smoking, diabetes and emotional stress.

The maintenance of blood pressure is highly complex and is dependent upon intrinsic, reflex, hormonal, renal and microvascular control systems. The complexity in the control of blood pressure is dependent upon the interaction from each of the control systems.

Development of hypertension is also suggested to depend on other mechanisms, including antidiuretic hormone (ADH) and baroreceptor resetting. The antidiuretic hormone is produced in the pituitary gland and regulates blood pressure through vasoconstriction and resorption of water. The pituitary gland communicates with the hypothalamus through neural connections, and thus the ADH release is under control of hypothalamic function. It is known that the hypothalamus is an important link between psychological events during emotional stress. However, a clear connection between emotional stress factors and hypothalamic control, either directly through the sympathetic nervous system, or indirectly with ADH release, has not been established.

Another mechanism leading to hypertension is that it is possible that the baroreceptor reflexes could be reset to maintain an elevated blood pressure for an indefinite time. There is suggested that there is no long term baroreceptive control and that resetting to a new level may occur. If baroreceptors are subjected to a maintained high pressure, their mean active rate returns to normal after a period of time. Evidences suggest that there may be a substantial resetting within as short time as 20 minutes.

In relation to the present invention the following US-patents may include valuable background information.

U.S. Pat. No. 6,275,733 discloses a dual sensor rate responsive pacemaker having an activity sensor, e.g. an acceleration-based sensor, and a metabolic sensor, such as a minute ventilation sensor. Determining the dual indicated rate is achieved by selecting between the two rates provided by these two sensors resulting in the use of the activity indicated rate during periods of low-level and brisk activity and the use of the metabolic indicated rate during periods of high exertion.

Another example of a dual sensor rate responsive pacemaker is disclosed in U.S. Pat. No. 6,055,454 relating to a cardiac pacemaker with automatic response optimization of a physiologic sensor based on a second sensor. The device has a first sensor for measuring a physiologic parameter reflecting metabolic demand and a second sensor for measuring a parameter reflecting the physical motion or activity of the patient, wherein the second sensor (activity sensor) is used to generate a dynamic target pacing rate which the first sensor is optimized to over time, thereby reducing the time constant for the adaptation of the first sensor and minimizing the amount of clinical time required to initialise the cardiac rhythm management device.

The normal physical response to the type of reactions mentioned above is an increase in blood pressure as well as an increase in heart rate. The same response may be observed when a person is preparing her- or himself for a significant physical activity.

In view of the above reasoning and in spite of all technical and physiological achievements in pacemaker technology of today, there is a need for a pacemaker responding to emotional reactions, emotional stress, such as nervousness, fear, joy, embarrassment and the like.

SUMMARY OF THE INVENTION

An object of the present invention is to provide an implantable heart stimulator that enables relevant reactions in emotional stress situations for a patient.

The above object is achieved in accordance with the present invention by an implantable heart stimulating device having a stimulation pulse generator connected to a lead arrangement to applied stimulation pulses to the heart of a patient, an activity sensor that senses activity by the patient and that emits an activity signal representing the sensed activity, and a physiological parameter sensor that senses or detects a physiological parameter of the patient and that emits a physiological sensor signal representative thereof. The activity and physiological sensor signals are supplied to a control arrangement that is configured to determine a stimulation rate by executing a stimulation rate algorithm dependent on the aforementioned signals. The execution of this stimulation rate algorithm, the control arrangement is configured to determined whether the physiological signal indicates emotional stress on the part of the patient and, if so, to increase the stimulation rate to an adjustable emotional stress rate level and, if no increase in the activity signal occurs during a predetermined time period following the stimulation rate increase, the control arrangement is configured to decrease the stimulation rate.

It is well-known that emotional stress for extended periods of time is detrimental to health.

The basis of the present invention is to increase the pacing rate if emotional stress is detected and also to slowly let the pacing rate go back to the baseline if no physical activity is detected.

This is achieved, according to a preferred embodiment of the invention, by identifying if the emotional stress component is much larger than an activity component. This is achieved by a control unit using an improved activity algorithm, herein referred to as a stimulation rate algorithm. In that case there would be a relatively rapid rate increase and the rate would then relatively slowly decrease to an intermediate stimulation rate depending on the relation between physical activity and emotional stress.

According to another preferred embodiment the rate will not drop all the way to the baseline if only emotional stress is detected.

In addition, a rate blending means is included to appropriately take into account, i.e. to blend, the influence from the activity and from the emotional stress, e.g. such that a very low physical activity but a high emotional stress will give a high rate initially but a limited rate increase in the long term.

Some research attempts have been made in the past to develop drugs to limit the heart rate reactions due to emotional stress. This may instead, by using the present invention, be readily implemented in a pacemaker capable of detecting emotional stress.

For patients having spontaneous heart rates that are increased due to emotional stress it would be possible, by using the present invention, to provide vagal stimulation in order to reduce the heart rate caused by the emotional stress. This could be achieved in a rate responsive pacemaker as well as in a non responsive device having a feature intended to limit the effects of emotional stress.

Thus, the present invention relates to a heart stimulating device comprising an activity sensor adapted to generate an activity signal in response of detected activity, and a physiological sensor, adapted to generate a physiological signal in response of a detected physiological parameter. The physiological sensor may be responsive of blood pressure, heart wall acceleration, impedance measurements, etc.

The activity and physiological signals are applied to a control means adapted to determine a stimulation heart rate based upon a stimulation rate algorithm and in dependence of those signals. More specifically, the control means includes an activity rate control means, an emotional rate control means, a response control means and a rate blending means.

If the patient is exposed to an emotional load or is preparing for a significant physical activity, the blood pressure would suddenly rise (within 2-10 heart beats), but the activity sensor would not perceive any activity. According to the present invention the pacing rate is then increased by a preset value, and if activity starts within a predetermined period of time, the activity sensor takes over the rate control. But if no activity is detected, the pacing rate is smoothly stepped down to a basic rate.

DESCRIPTION OF THE PREFERRED EMBODIMENTS

The invention will now be described in greater detail with references to the figures.

Figure 1:
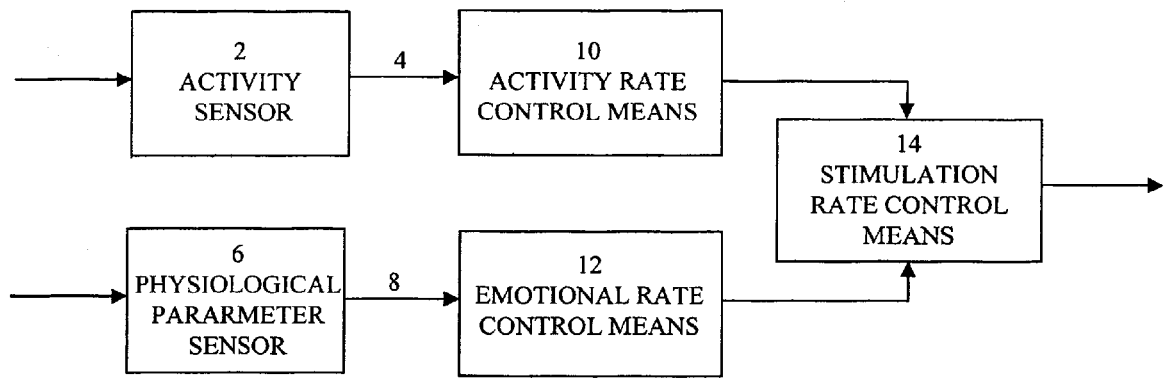
FIG. 1 is a schematic block diagram illustrating an embodiment of the present invention.
Figure 2:
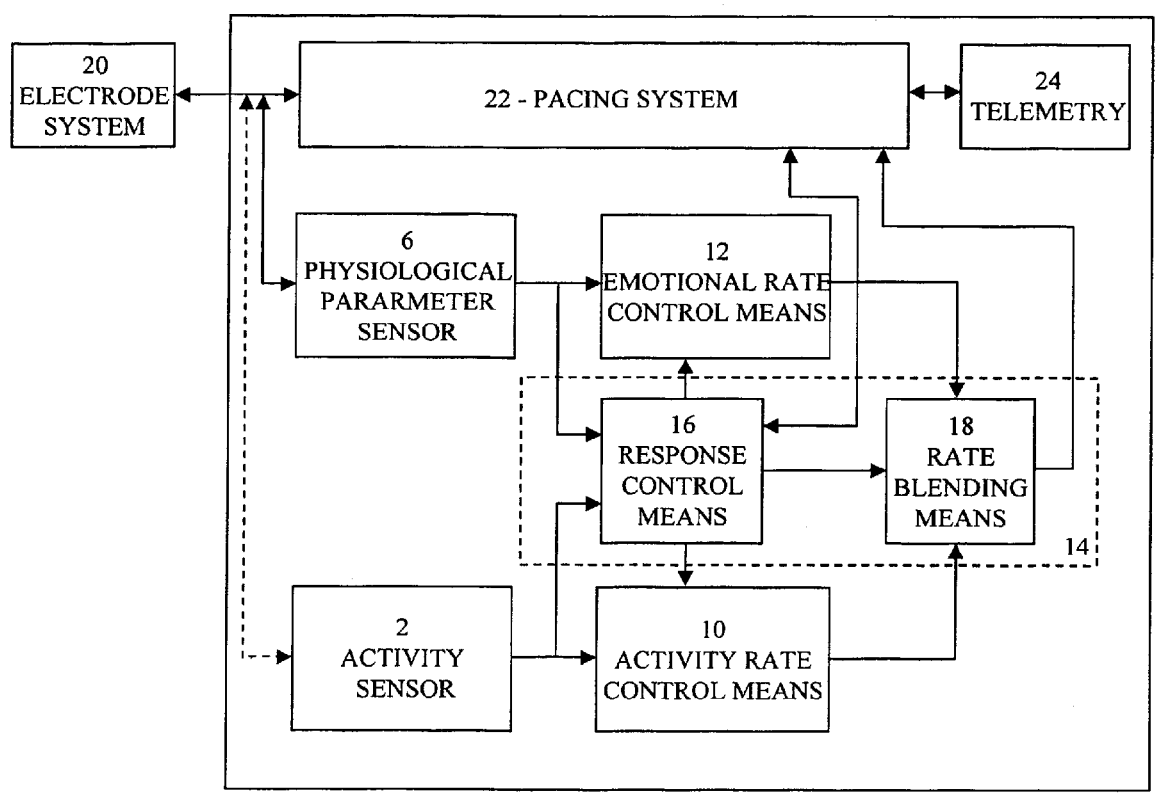
FIG. 2 is a schematic block diagram illustrating, in greater detail, the preferred embodiment illustrated in FIG. 1.

FIG. 1 is a block diagram generally illustrating the essential features of the present invention being a part of an implantable heart stimulating device generally illustrated by the block diagram of FIG. 2.

With references to FIGS. 1 and 2, the present invention relates to an implantable heart stimulating device adapted to generate stimulation pulses at a stimulation rate to be applied to a patients heart, comprising an activity sensor 2, generating an activity signal 4 in response of detected activity of the patient, and a physiological parameter sensor 6, e.g. a pressure sensor, generating a physiological sensor signal 8 in response of a detected physiological parameter.

The activity and physiological sensor signals are applied to a control arrangement formed by units 10, 12, 14 that are configured to determine a stimulation rate based upon a stimulation rate algorithm in dependence of those signals, wherein if the physiological signal indicates an emotional stress for the patient, the stimulation rate is increased to an adjustable emotional stress rate level and if no increase of the activity signal is indicated, during a predetermined time period from the stimulation rate increase, the stimulation rate is decreased.

The control arrangement includes an activity rate control unit 10, an emotional rate control unit 12 and a stimulation rate control unit 14. The stimulation rate control unit 14 includes, in its turn, a response control unit 16 and a rate blending unit 18.

In one preferred embodiment the emotional stress stimulation rate increase is 10-30 stimulations per minute during a period of 30-50 seconds, and the emotional stress stimulation rate decrease is 10-20 stimulations per minute during a first decrease interval of 50-70 seconds, and 60-80 stimulations per minute during a second decrease interval of 5-15 seconds.

As appreciated by the skilled person in the field of implantable pacemakers, the implantable heart stimulating device further includes a pacing system 22 that includes all necessary components and circuitry to achieve the heart stimulation functions, e.g. further control circuitry, e.g. a microprocessor, and a battery. The pacing system is connected to a telemetry unit 24, responsive for wireless communication between the implanted device and an external programming device (a programmer), in accordance with well-known procedures. An electrode system 20 is connectable to the implantable heart stimulating device, also in accordance with well-known techniques. The electrode system 20 may include one or many heart electrode leads, arranged to be able to perform monopolar or bipolar stimulation of the heart, and each electrode lead may include one or many stimulation electrode surfaces. The electrode lead is adapted to be arranged to perform stimulation in the right and/or left part of the heart, and may e.g. be inserted, by using well-known techniques, in the coronary sinus to perform left ventricle stimulation.

The activity sensor 2 may be arranged inside the housing of the implantable heart stimulating device, or may be arranged in connection with the electrode system, e.g. close to the distal end of an electrode lead.

The physiological parameter sensor 6 is preferably a pressure sensor, responsive of blood pressure, that advantageously also may be arranged close to the distal end of an electrode lead.

According to an alternative embodiment the physiological sensor is responsive of heart wall acceleration or of impedance measurements.

The influence of the emotional stress level is such, in accordance with the stimulation rate algorithm, that the algorithm only takes the emotional stress level into account if the present heart rate is less than a predetermined heart rate, preferably 100 beats per minute (bpm). The stimulation rate increase, related to the emotional stress level, is only possible if the activity signal is below a preset level. At higher activity levels the stimulation rate algorithm favors the influence from the patient's activity level.

Figure 3:
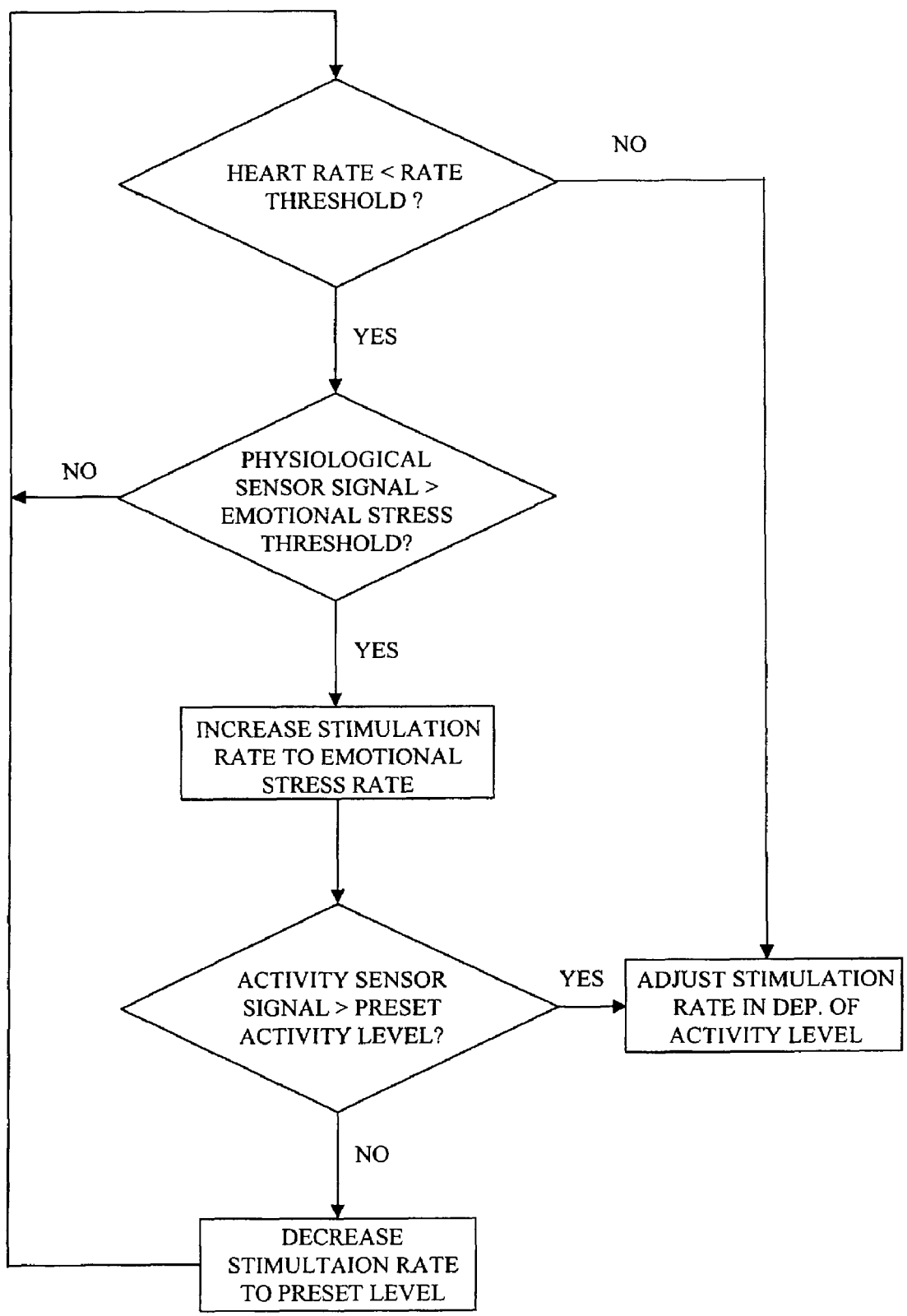
FIG. 3 is a schematic flow diagram generally illustrating the present invention.

FIG. 3 is a schematic flow diagram generally illustrating the present invention.

The present heart rate is compared to a predetermined rate threshold, e.g. 100 bpm, and if the present heart rate is above that threshold the stimulation rate is adjusted in dependence of the activity level indicated by the activity sensor.

If the heart rate is below the threshold the physiological sensor signal is compared to an emotional stress threshold and if the comparison is affirmative the stimulation rate is increased up to a preset emotional stress heart rate during a predetermined time interval, e.g. less than one minute, and if the activity sensor indicates no activity, the stimulation rate is decreased down to the initial base level or to a level slightly above the base level.

If, however, the activity sensor indicates that the increased emotional stress level is followed by an increased activity level for the patient, the stimulation rate is adjusted in dependence on the activity level.

Figure 4:
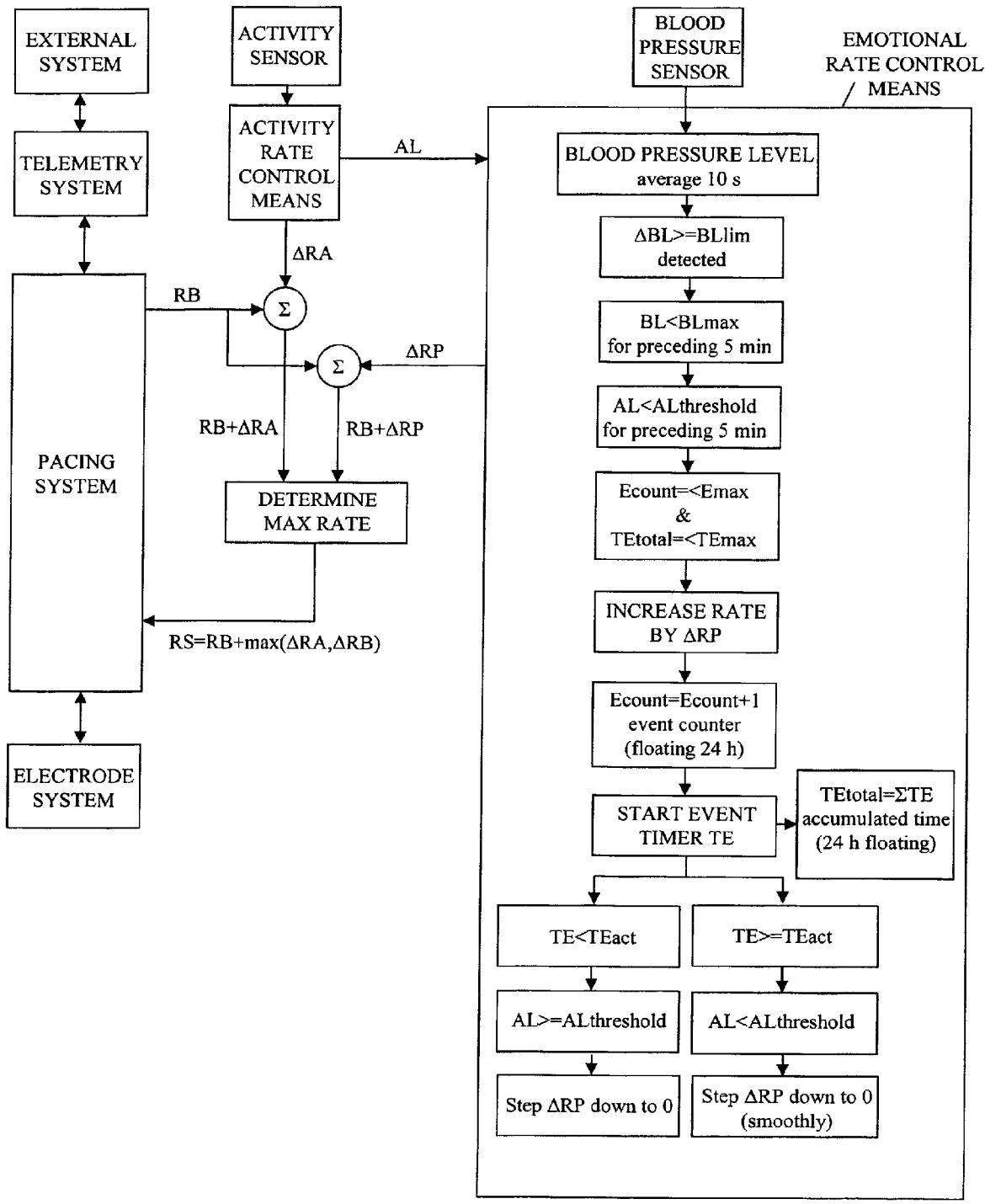
FIG. 4 is a detailed schematic illustration of a preferred embodiment of the present invention.

A block diagram illustrating a preferred embodiment of the present invention is shown in FIG. 4.

In this preferred embodiment the physiological parameter sensor is a pressure sensor.

The algorithm used to implement the present invention is only activated if a low or resting activity level for the patient is present. And in addition, no pressure-controlled stimulation is active during high detected or stimulated heart rates, e.g. 100 beats per minutes (bpm).

As in the other embodiments, the use and set-up of the algorithm is determined by external programming.

The left side of the block diagram illustrated in FIG. 4 shows a conventional pacemaker system including Pacing System, Electrode System, Telemetry System and External System (programmer).

The activity sensor and the activity rate control means are shown separate from the pacing system. The activity sensor output is averaged over a short time period, e.g. 10 seconds, to give a momentary Activity Level (AL) value, and the activity rate control means outputs a delta rate value $\Delta RA$ (the rate increase), which is added to the programmed base rate RB. This processing is well known from conventional rate responsive pacemaker systems.

Also shown is the physiological parameter sensor, in this case a blood pressure sensor, and the emotional rate control means having a set of programmable registers (not shown) that includes values used by the algorithm and programmable via the external programmer.

In the following, blood pressure values are used that assumes that the pressure sensor is located in the right ventricle, but other locations and other values may of course be of interest.

The Blood Pressure Sensor is connected to a short time average register, which outputs a Blood Pressure Average value BL. A check is then performed to detect if the blood pressure has undergone a level increase of at least $\Delta BLlim$, e.g. 5 mmHg. If this is the case, a number of conditions must be satisfied in order to activate the blood pressure rate control:

The blood pressure level should have been below a maximum limit BLmax (e.g. 20 mmHg) for a specified time period Tinactive, (e.g. 5 min).

The activity level should have been below a maximum limit ALthreshold (e.g. 5% of ALmax) for a specified time Tinactive.

The number of rate increases Ecount (events) due to blood pressure should not exceed a maximal limit Emax during a time period, for instance 24 h.

The total blood pressure TEtotal controlled activation time should not exceed a maximal limit TEmax during a time period, for instance 24 h.

If all above conditions are fulfilled, the blood pressure rate control starts which adds a $\Delta RP$ value to the programmed basic rate. The activity level and blood pressure level is then checked during an activation time TEact.

If the activity level do not pass the activity threshold ALthreshold during this time (lower left path) the response is considered emotional without any following body activity. The rate increase $\Delta RP$ is then smoothly stepped down to the basic rate.

If the activity level passes the activity threshold during TEact (lower right path), response is considered emotional, when the patient is preparing for an activity. The conventional activity rate control then takes over the rate control which adds a $\Delta RA$ value to the programmed basic rate, while $\Delta RP$ is stepped down to basic rate.

The maximum of $\Delta RP$ and $\Delta RA$ is selected in order to ensure smooth transitions between the activity and pressure control of the heart rate.

The emotional rate control means is controlled by the pacing system via the response control arrangement (see FIG. 2).

It is an object of the present invention to achieve an emotional rate control of the heart rate which mimics the natural response. That is the reason why the emotional rate control is not active during high heart rate and/or high blood pressure.

Figure 5:
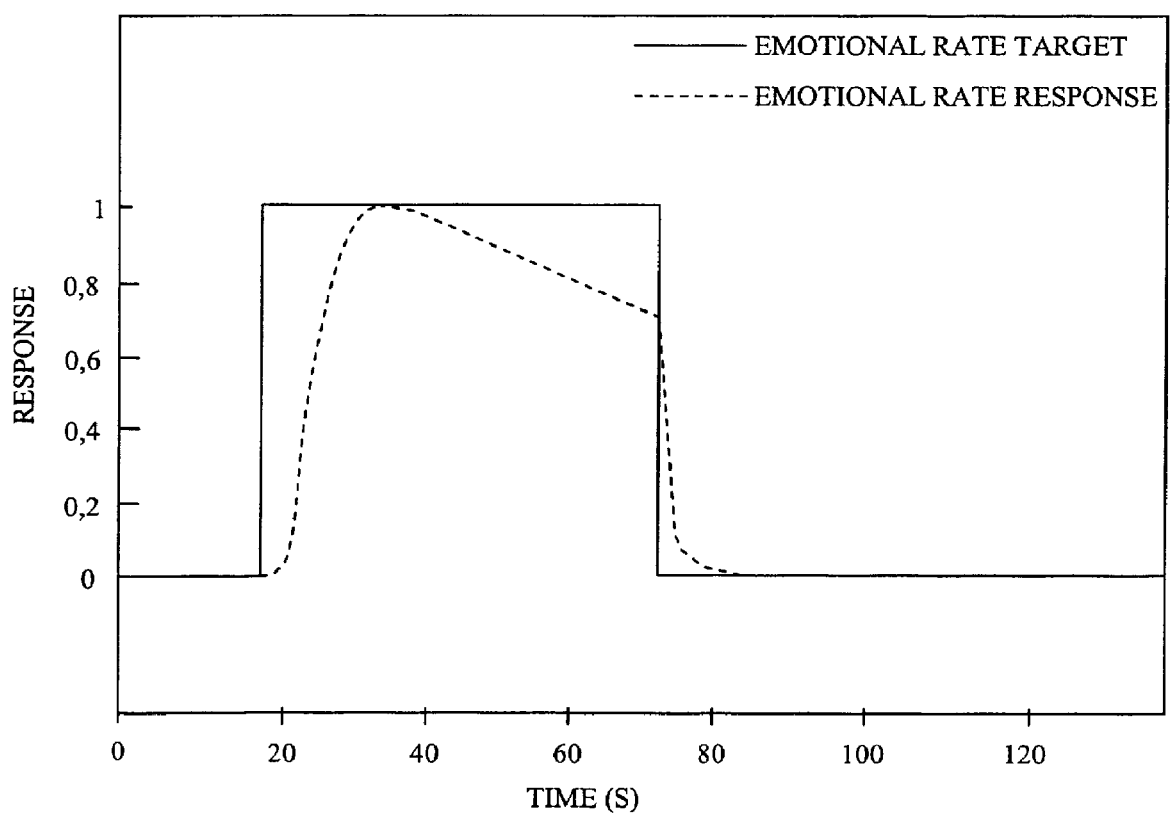
FIG. 5 shows a graph that schematically illustrates the emotional rate response for a given exemplary constant emotional sensor value according to the present invention.

FIG. 5 shows a graph that schematically illustrates the emotional rate response for a given exemplary constant emotional sensor value. The x-axis denotes the time in seconds and the y-axis denotes the response in an arbitrary unit. The emotional target rate represents a rate increase from a base rate in response of predetermined input emotional sensor value from the physiological parameter sensor. The emotional sensor value is detected just before 20 s. The value "1" may represent a rate increase of 20 stimulations per minute (PPM) for a systolic pressure increase, for instance 20 mmHg of aortic pressure. The dashed line is the output from the emotional rate control means. It reaches the maximal rate around 35 s in this example and decreases thereafter. A much faster rate decrease is applied just after 70 s when the emotional sensor value returns to the base level.

An exemplary illustration of how useful the present invention may be illustrated by the situation that occurs when a patient is at rest but is about to prepare for a coming body activity, e.g. feels emotions for leaving bed in order to go to the nearby local storage. The emotional rate control means will then respond by a first rate increase and the activity rate control means will then, when the activity is initiated, take over more and more of the rate control, as blended by the rate blending means.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable heart stimulation device comprising:
   a stimulation pulse generator that emits stimulation pulses at an adjustable stimulation rate that is normally at a base rate;
   an implantable lead arrangement connected to the stimulation pulse generator configured to deliver the stimulation pulses to the heart of a patient;
   an activity sensor that detects an activity level of the patient and emits an activity signal representing said activity level;
   a physiological parameter sensor that detects a parameter representing a physiological characteristic of the patient and that emits a physiological sensor signal representing said parameter; and
   a control arrangement configured to receive a signal indicative of a heart rate of the patient and execute a stimulation rate algorithm to set the stimulation rate for said stimulation pulse generator, said control arrangement being configured to first determine whether the heart rate of the patient is below a predetermined heart rate and only if so to continue to execute said stimulation rate algorithm by determining whether said physiological sensor signal indicates an existence of emotional stress of the patient by being above a predetermined emotional stress threshold and, if so, to increase said stimulation rate to a predetermined emotional stress rate level and, if no increase in said activity signal occurs during a predetermined time period following increasing said stimulation rate, to decrease said stimulation rate substantially to said base rate and, if said activity level is above a predetermined activity level, to adjust said stimulation rate dependent on said activity level.

2. An implantable heart stimulating device as claimed in claim 1 wherein said control arrangement is configured to employ 100 beats per minute as said predetermined heart rate.

3. An implantable heart stimulating device as claimed in claim 1 wherein said physiological parameter sensor is a blood pressure sensor.

4. An implantable heart stimulating device as claimed in claim 1 wherein said physiological parameter sensor is a heart wall acceleration sensor.

5. An implantable heart stimulating device as claimed in claim 1 wherein said physiological parameter sensor is an impedance sensor.

6. An implantable heart stimulating device as claimed in claim 1 wherein said control arrangement is configured to increase said stimulation rate up to said predetermined emotional stress rate level by increasing said stimulation rate between 10 and 30 stimulation pulses per minute during 30 to 50 seconds.

7. An implantable heart stimulating device as claimed in claim 1 wherein said control arrangement is configured to decrease said emotional stress stimulation rate level between 10 and 20 stimulation pulses per minute during a first decrease interval of 50 to 70 seconds, and between 60-80 stimulation pulses per minute during a second decrease interval of 5 to 15 seconds.

8. An implantable heart stimulating device as claimed in claim 1 further comprising a vagal stimulation pulse generator and a vagal stimulation lead connected thereto, configured to deliver vagal stimulation pulses to the vagal nerve of the patient, and wherein said control arrangement is configured to operate said vagal stimulation pulse generator to decrease said stimulation rate.

* * * * *